United States Patent
Shibuya et al.

(10) Patent No.: US 8,090,170 B2
(45) Date of Patent: Jan. 3, 2012

(54) MEDICAL IMAGE STORAGE DEVICE

(75) Inventors: Masato Shibuya, Otawara (JP); Kenichi Niwa, Otawara (JP); Hirobumi Nonaka, Yaita (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 851 days.

(21) Appl. No.: 12/039,237

(22) Filed: Feb. 28, 2008

(65) Prior Publication Data

US 2008/0212855 A1  Sep. 4, 2008

(30) Foreign Application Priority Data

Mar. 2, 2007 (JP) ................... 2007-052878

(51) Int. Cl.
*G06K 9/00* (2006.01)
(52) U.S. Cl. .................................. 382/128
(58) Field of Classification Search .............. None
See application file for complete search history.

(56) References Cited

U.S. PATENT DOCUMENTS

2005/0108060 A1* 5/2005 Sasano ............... 705/3

FOREIGN PATENT DOCUMENTS

| JP | 2002-360519 | 12/2002 |
|---|---|---|
| JP | 2006-15125 | 1/2006 |
| JP | 2006-68444 | 3/2006 |
| JP | 2006-280598 | 10/2006 |
| WO | WO 2006/040258 A2 | 4/2006 |

OTHER PUBLICATIONS

U.S. Appl. No. 12/062,209, filed Apr. 3, 2008, Minakuchi et al.
U.S. Appl. No. 12/196,728, filed Aug. 22, 2008, Niwa et al.
Li Zhuo, et al., "Data Organizing and Medical Image Series Generating Based on DICOM Standard", Computer Processes and Applications, vol. 8, Aug. 2005, pp. 221-223.

* cited by examiner

*Primary Examiner* — Tom Y Lu
(74) *Attorney, Agent, or Firm* — Oblon, Spivak, McClelland, Maier & Neustadt, L.L.P.

(57) ABSTRACT

A medical image observation device relating to the present invention receives enhanced image data having a plurality of medical images, and splits the enhanced image data into a plurality of single image data each containing only one medical image, based on system information of the enhanced image data. According to the present invention, it is possible to make a medical image observation device accurately display an image without depending on system information of enhanced image data.

14 Claims, 8 Drawing Sheets

| IMAGE ATTRIBUTE INFORMATION | SYSTEM INFORMATION | |
|---|---|---|
| MODALITY | Stc ID | Tindex |
| MR | Series | IMAGE ID |
| CT | IMAGE ID | Series |
| ⋮ | ⋮ | ⋮ |

MEDICAL IMAGE STORAGE DEVICE

BACKGROUND OF THE INVENTION

1. Field of the Invention

The present invention relates to a medical image storage device configured to store a medical image.

2. Description of the Related Art

A medical image storage device is a device for storing a medical image of a subject body site or the like captured by a medical imaging device (modality) such as an X-ray tomographic imaging device (CT) and a magnetic resonance imaging device (MRI). This medical image storage device is connected to a medical imaging device, a medical-report creation supporting device and a medical image observation device via a network such as a LAN, whereby a medical image storage system (medical picture archiving communication system, PACS) is configured.

Image data generated by a medical imaging device normally complies with the DICOM (Digital Imaging and Communication in Medicine) standard established by the American College of Radiology (ACR) and National Electrical Manufacturers Association (NEMA). A medical image observation device displays a medical image based on image data provided by the DICOM standard. This image data is stored and managed by the medical image storage device. Medical image storage devices are disclosed in, for example, Japanese Unexamined Patent Application Publication No. 2006-68444, Japanese Unexamined Patent Application Publication No. 2006-280598, and Japanese Unexamined Patent Application Publication No. 2006-15125. With these disclosed techniques, image data is classified and stored on a series-by-series basis.

Although single image data having only one image is generally used as image data, enhanced image data in which a plurality of images are linked is used recently for the purpose of sending and receiving a large number of images.

Here, the single image data is image data in which incidental information is linked to one tomographic image, image data in which the SOP class name of the DICOM standard is "CT Image Storage" and the SOP class UID is "1.2.840.10008.5.1.4.1.1.2," or the like. On the other hand, the enhanced image data is image data in which common incidental information is linked to a plurality of tomographic images, image data in which the SOP class name of the DICOM standard is "Enhanced CT Image Storage" and the SOP class UID is "1.2.840.10008.5.1.4.1.2.1," or the like In many cases, the systems of enhanced image data vary depending on the types, manufactures and versions of modalities serving as data generating devices. This system is represented by stack information (Stack ID), index information (Temporal Index,) or the like. To be specific, it is represented by a Stack ID (0020, 9056) or a Temporal Position Index (0020, 9128). Difference of the systems means difference of the meanings and contents represented by the stack information and index information. For example, as for enhanced image data created by a CT device, the stack information represents the image ID, and the index information represents the series ID. On the other hand, as for enhanced image data created by an MRI device, the stack information represents the series ID, and the index information represents the image ID.

However, in a case where the systems of enhanced image data vary depending on the types, manufacturers and versions of modalities, the system of the enhanced image data received by a medical image observation device may be different from the system of recognizable enhanced image data. Therefore, there is a possibility that the medical image observation device is incapable of properly recognizing the enhanced image data, and hence, is incapable of accurately displaying a medical image. Moreover, an old-type medical image observation device does not comply with enhanced image data, and cannot accurately display a medical image contained in the enhanced image data.

SUMMARY OF THE INVENTION

An object of the present invention is to provide a medical image storage device that enables a medical image observation device to accurately display an image without depending on the system of enhanced image data.

When receiving enhanced image data having a plurality of medical images, a medical image observation device relating to the present invention splits the received enhanced image data into a plurality of single image data each having only one medical image, based on the system information of the received enhanced image data. According to the present invention, the medical image observation device can accurately display images without depending on the system of enhanced image data.

DETAILED DESCRIPTION OF THE EMBODIMENT

An embodiment of the present invention will be described referring to the drawings.

Figure 1:
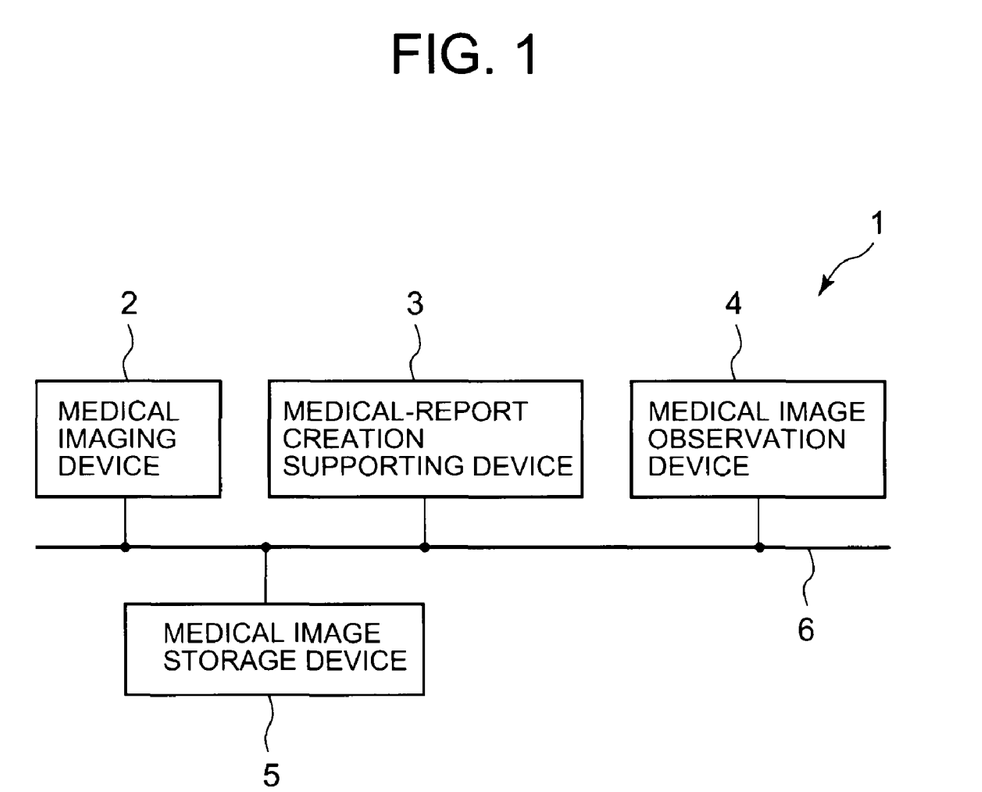
FIG. 1 shows a schematic configuration of a medical image storage system relating to an embodiment of the present invention.

As shown in FIG. 1, a medical image storage system 1 relating to the embodiment of the present invention comprises: a medical imaging device 2 configured to capture a medical image of a subject such as a patient; a medical-report creation supporting device 3 configured to support creation of a medical report; a medical image observation device 4 such as a viewer configured to display a medical image; and a medical image storage device 5 configured to store a medical image captured by the medical imaging device 2. These devices are connected to each other via a network 6 such as a LAN (Local Area Network).

The medical imaging device 2 is a modality capturing medical images of sites of a subject body. The medical imaging device 2 sends image data (e.g., tomographic image data) regarding a captured medical image to the medical image storage device 5. As the medical imaging device 2, it is possible to use various types of modalities such as a CT device and an MRI device.

The medical-report creation supporting device 3 is a device for creating a medical report used by a user such as a doctor at the time of creation of a medical report such as a diagnostic finding report. The user observes a medical image displayed by the medical image observation device 4, and creates a medical report by using the medical-report creation supporting device 3. The medical report is stored in the medical-report creation supporting device 3, for example.

The medical image observation device 4 receives image data sent from the medical image storage device 5, and displays a 2-dimensional medical image based on the received image data. Further, the medical image observation device 4 generates volume data for a 3-dimensional image from the received image data, and displays a 3-dimensional medical image based on the generated volume data. To be specific, the medical image observation device 4 applies, to the volume data, image processing such as a volume-rendering process, an MPR (Multi Planer Reconstruction) process and an MIP (Maximum Intensity Projection) process, generates image data for display, and displays a medical image based on the image data.

Figure 2:
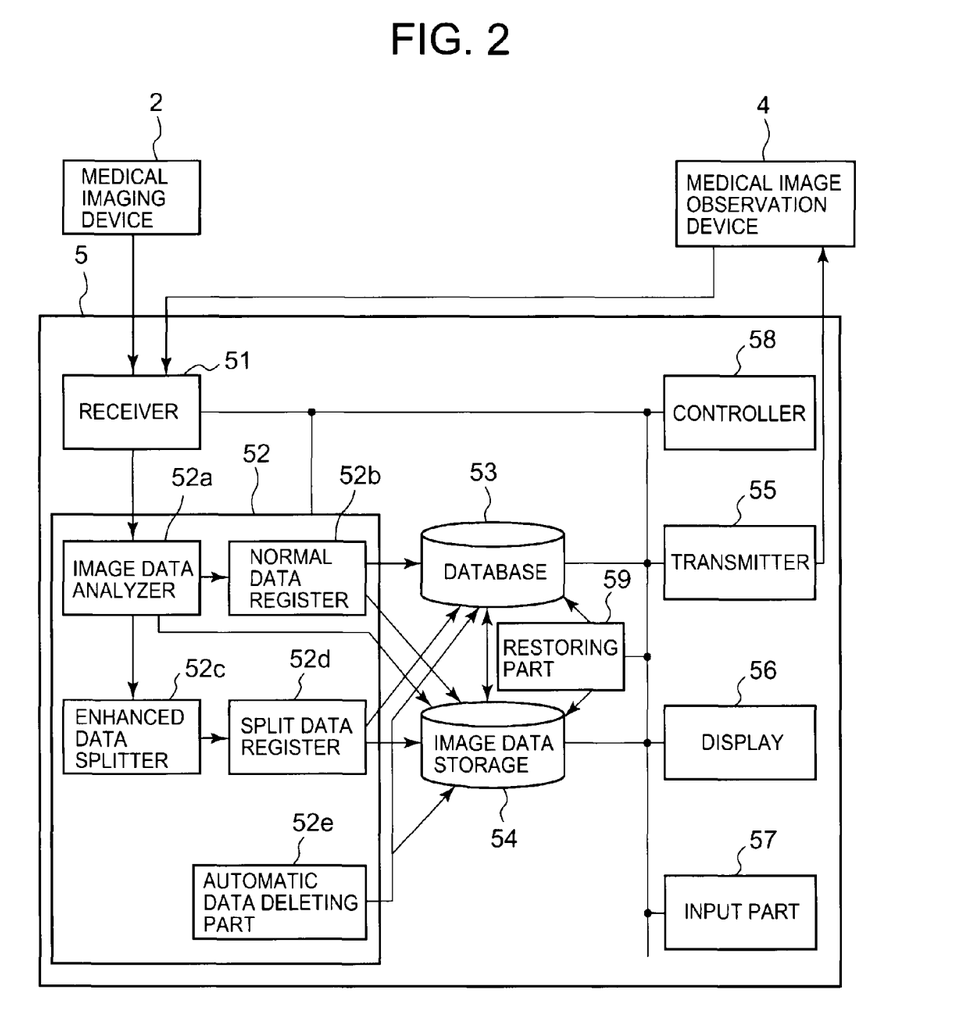
FIG. 2 shows a schematic configuration of a medical image storage device provided in the medical image storage system.

As shown in FIG. 2, the medical image storage device 5 comprises: a receiver 51 configured to receive image data sent from the medical imaging device 2, an image display request sent from the medical image observation device 4, and the like; an image storage processor 52 configured to execute a storing process for the received image data; a database 53 configured to store various types of data; an image data storage 54 configured to store image data; a transmitter 55 configured to send various types of data such as image data to the medical image observation device 4; a display 56 configured to display a medical image; an input part 57 configured to receive an input operation from a user that is an operator; a controller 58 configured to control the respective parts; and a restoring part 59 configured to restore enhanced image data D1 from split single image data D2.

The image storage processor 52 comprises: an image data analyzer 52a configured to analyze the received image data; a normal data register 52b configured to register normal image data into the database 53 and the image data storage 54; an enhanced data splitter 52c configured to split the enhanced image data D1 into a plurality of single image data D2; a split data register 52d configured to register the respective single image data D2 obtained by splitting, into the database 53 and the image data storage 54; and an automatic data deleting part 52e configured to automatically delete various types of data stored in the database 53 and the image data storage 54.

Figure 3:
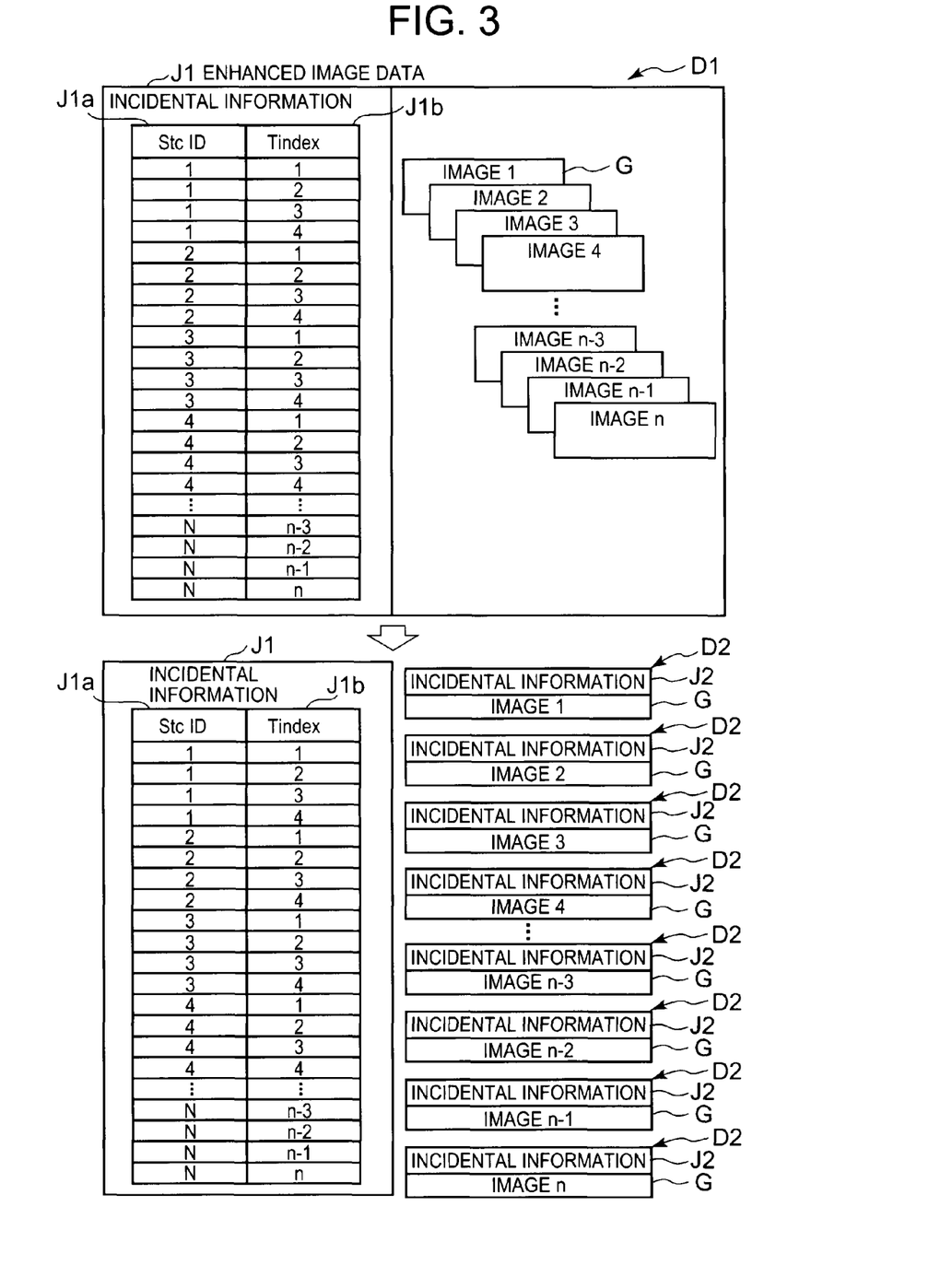
FIG. 3 is a view for explaining a splitting process executed by an enhanced data splitter provided in the medical image storage device.

Here, as shown in FIG. 3, the enhanced image data D1 is image data including a plurality of images G and common incidental information J1 linked to these images G. The images G are linked and unified into an aggregate of the images G, and written in as, for example, pixel data. Further, the incidental information J1 represents patient information on patients, information representing examination information on examinations, and the systems of the plurality of included images. The systems are represented by, for example, stack information J1a and index information J1b. For example, the stack information J1a represents a series ID that is the identification number of a subject body site in enhanced image data D1 derived from an MRI device, and represents an image ID in enhanced image data D1 derived from a CT device. For example, the index information J1b represents an image ID in enhanced image data D1 derived from an MRI device, and represents a series ID that is the number of a subject body site in enhanced image data D1 derived from a CT device. The enhanced image data D1 is, for example, image data in which the SOP class name of the DICOM standard is "Enhanced CT Image Storage" and the SOP class UID is "1.2.840.10008.5.1.4.1.2.1."

On the other hand, the single image data D2 is image data having only one image G and incidental information J2 linked to the image G. The image G is written in as, for example, pixel data. Further, the incidental information J2 is information including patient information on a patient, examination information on an examination, information for identifying the image G included in the single image data D2, or the like. For example, the incidental information J2 is information including a tag number, a patient ID, a series ID, or an image ID. The medical image observation device 4 displays the images G in the accurately arranged state in accordance with information for identifying the positioning of images G such as the series ID and image ID. The single image data D2 is provided by the DICOM standard. The single image data D2 is, for example, image data in which the SOP class name of the DICOM standard is "CT Image Storage" and the SOP class UID is "1.2.840.10008.5.1.4.1.1.2."

Returning to FIG. 2, the image data analyzer 52a determines whether the received image data is the enhanced image data D1. In the case of determining that the received image data is the enhanced image data D1, the image data analyzer 52a outputs the image data to the enhanced data splitter 52c as the enhanced image data D1. In the case of determining that the received image data is not the enhanced image data, the image data analyzer 52a outputs the image data to the normal data register 52b as normal image data (single image data D2).

The normal data register 52b registers normal image data (single image data D2) inputted from the image data analyzer 52a, into the database 53 and the image data storage 54. To be specific, the normal image data register 52b registers normal image data and incidental information into the image data storage 54, and registers a file path indicating a storage destination into the database 53.

Based on system information J4 of the received enhanced image data D1, as shown in FIG. 3, the enhanced data splitter 52c splits the received enhanced image data D1 into a plurality of single image data D2, and outputs the plurality of single image data D2 obtained by splitting to the split data register 52d. To be specific, the enhanced data splitter 52c interprets the system of the enhanced image data D1 with reference to the system information J4, and attaches information for identifying the positioning of the image G2 obtained by splitting. In other words, in accordance with the system information J4, the stack information J1a and the index information J1b are included in the incidental information J2 of the single image data D2, as one of a series ID and an image ID and as the other of the series ID and the image ID, respectively. Furthermore, the enhanced data splitter 52c registers the received enhanced image data D1 as it is in the image data storage 54.

This enhanced data splitter 52c having a system information table T (refer to FIG. 4) specifies the system information J4 corresponding to image attribute information J3 of the received enhanced image data D1, based on the system information table T, and splits the received enhanced image data D1 into a plurality of single image data D2, based on the specified system information J4. The image attribute information J3 is included in the incidental information J1 of the received enhanced image data D1.

Figure 4:
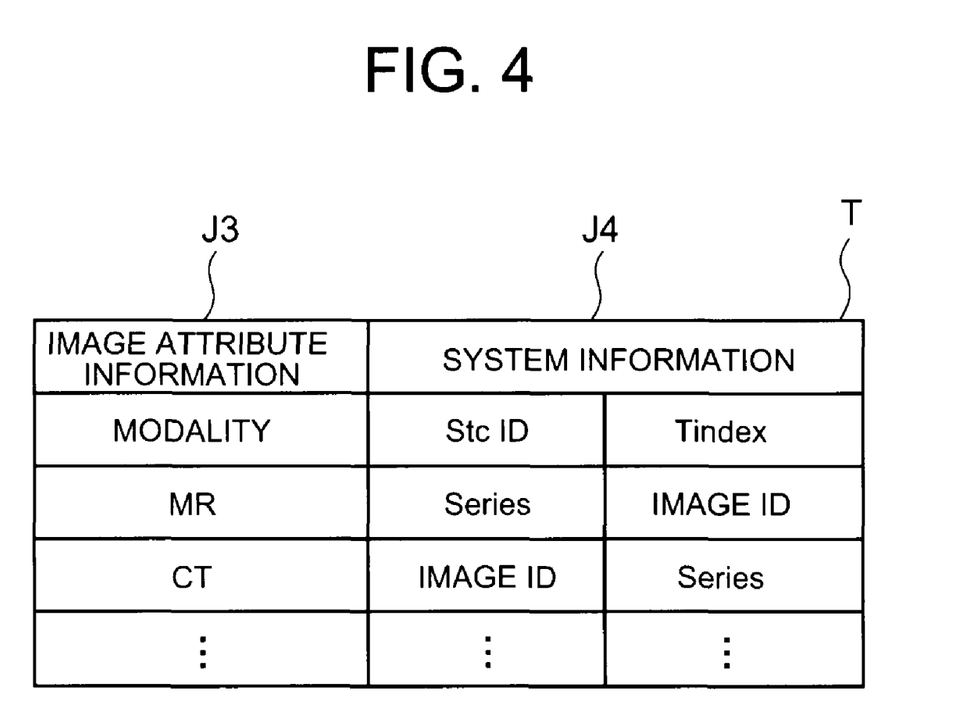
FIG. 4 is a view for explaining a system information table used by the enhanced data splitter provided in the medical image storage device.

In the system information table T, as shown in FIG. 4, the system information J4 is registered in association with the image attribute information J3. This system information table T is previously set, and becomes information associating the image attribute information J3 with the system information J4. The image attribute information J3 is information representing image attributes, which is information representing modalities such as CT and MR. Other than modalities, the image attribute information J3 may be, for example, manufacturers, model names, software versions, AE titles, communication information (AE titles, IP addresses, etc.), image types, and furthermore, combination thereof. Moreover, the system information J4 is information representing the meaning and content of the system of the enhanced image data D1. For example, the system information J4 is information representing what the stack information (Stack ID) J1$a$ and the index information (Tindex) J1$b$ mean, respectively.

Because the enhanced image data D1 includes the system information J4, namely, classification methods that vary depending on the image attribute information J3, classification units are determined so as to correspond to the system information J4. Therefore, the enhanced data splitter 52$c$ splits the enhanced image data D1 into a plurality of single image data D2 so that the plurality of single image data D2 can be managed on the basis of classification units provided by the system information J4.

For example, in a case where the image attribute information J3 of the received enhanced image data D1 is MR, system information J4 in which StcID is a series ID and Tindex is an image ID is used. In this case, the classification unit is a series unit. On the other hand, in a case where the image attribute information J3 of the received enhanced image data D1 is CT, system information J4 in which StcID is an image ID and Tindex is a series ID is used. In this case, the classification unit is an image ID unit. Since the respective single image data D2 are thus managed by classification units provided by the system information J4, it is possible to respond even when the medical image observation device 4 requests medical images by classification units.

In addition, the enhanced data splitter 52$c$ corrects the incidental information J2 of the single image data D2. An example of this correction is correction of appropriately embedding information such as a window level, window width and image position into appropriate positions in the incidental information J2. Moreover, the enhanced data splitter 52$c$ outputs the incidental information (original incidental information) J1 of the enhanced image data D1 to the split data register 52$d$. The incidental information J1 of the enhanced image data D1 is required at the time of restoration of a plurality of single image data D2 to the original enhanced image data D1.

Returning to FIG. 2, the split data register 52$d$ registers the plurality of single image data D2 and the incidental information J1 of the enhanced image data D1 inputted from the enhanced data splitter 52$c$, into the database 53 and the image data storage 54. To be specific, the split data register 52$d$ registers the plurality of single image data D2, and the incidental information J1 of the enhanced image data D1 in association with the single image data D2, into the image data storage 54, and registers file paths into the database 53.

The automatic data deleting part 52$e$ deletes unnecessary image data from the image data storage 54, based on set information representing a period set in advance (e.g., about one month) or the like. For example, in a case where the image data is single image data D2, the automatic data deleting part 52$e$ deletes an image G of the single image data D2 having been stored for a predetermined period, corrects inconsistencies of the incidental information J1 of the enhanced image data D1 corresponding to the single image data D2 of the deleted image G, and furthermore, updates the database 53. In addition, the automatic data deleting part 52$e$ deletes enhanced image data D1 having been stored for a predetermined period, based on set information representing a period set in advance (e.g., about one month) or the like, whereby a storage space is secured. In correction of inconsistencies, specifically, the automatic data deleting part 52$e$ deletes information for identifying the positioning of the image ID, series ID and the like corresponding to the deleted image G, from the incidental information J1, and advances information for identifying the positioning of an image G positioned after the deleted image G. The set information is stored in the database 53 or in a memory or the like provided in the controller 58.

Figure 5:
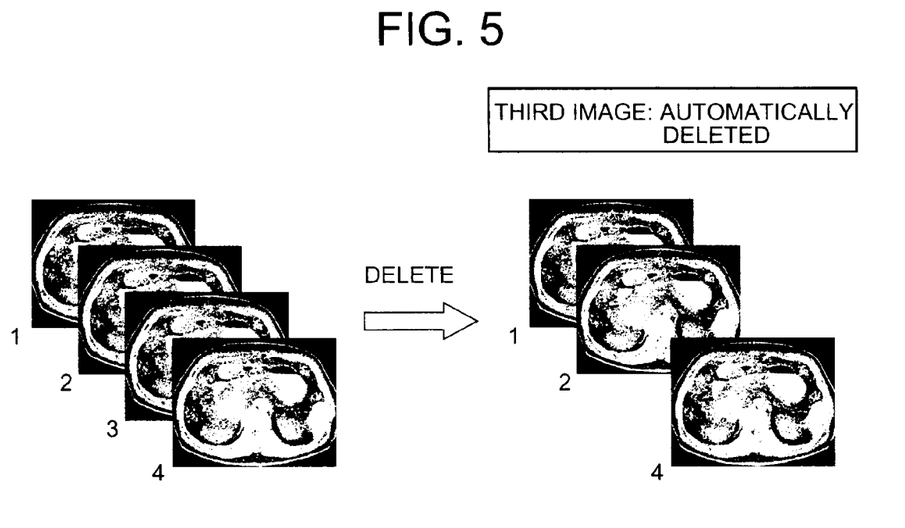
FIG. 5 is a view for explaining an automatic deletion process performed by an automatic data deleting part provided in the medical image storage device.
Figure 6:
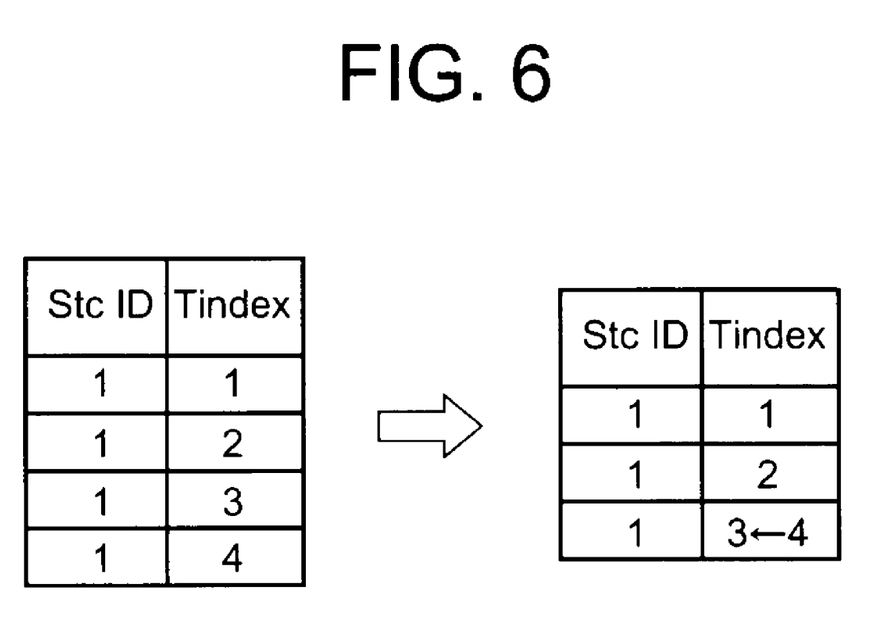
FIG. 6 is a view for explaining an inconsistency resolution process in the automatic deletion process performed by the automatic data deleting part provided in the medical image storage device.

Herein, for example, as shown in FIG. 5, when an image 3 is deleted by the automatic data deleting part 52$e$, only images 1, 2 and 4 are left. At this moment, because the image 3 has been deleted, as shown in FIG. 6, the image ID of the image 4 replaces the image ID of the image 3, and the incidental information J1 of the enhanced image data D1 is rewritten. Consequently, inconsistencies in the incidental information J1 of the enhanced image data D1 are resolved. In an actual display, as shown in FIG. 5, in addition to displaying the images 1, 2 and 4, text such as "third image: automatically deleted" is displayed. Such text is displayed based on deletion information, and the user is informed that the image 3 has been deleted. The deletion information is information for specifying single image data D2 of the deleted image and, for example, is embedded into series comment information within the incidental information J2 of the single image data D2. The deleted information may be stored in the database 53.

Returning to FIG. 2, the database 53 is a database configured to manage specification information for specifying managed examinations, storage positions of image data, or the like. For example, the database 53 stores the file paths of various types of data such as enhanced image data D1 and single image data D2 having been registered in the image data storage 54.

The image data storage 54 receives image data such as enhanced image data D1 and single image data D2, and writes and stores into an appropriate position. Further, the image data storage 54 communicates with the database 53 and makes corrections of the database 53—e.g., when a storage position has been determined, when image data of a storage position has been deleted, or when a storage position has been changed. As the image data storage 54, a hard disk drive, a NAS (Network Attached Storage) or the like may be used.

The transmitter 55 and the receiver 51 are communication devices configured to communicate with external devices via a network 6 such as a LAN. Here, the external devices are the medical imaging device 2, the medical-report creation supporting device 3, and the medical image observation device 4. As the communication devices, a LAN card, a modem or the like is used.

The display 56 is a display device configured to display a medical image such as a tomographic image (a slice image) of a subject. As the display 56, for example, a liquid crystal display or a CRT (Cathode Ray Tube) display is used.

The input part 57 is an operation part used for input by the user, and is a device configured to receive various types of input operations such as starting display of an image display or switching images. As the input part 57, for example, an input device such as a mouse and a keyboard is used.

The controller 58 is provided with a CPU (Central Processing Unit) intensively controlling the respective parts, and a memory such as a ROM (Read Only Memory) and a RAM (Random Access Memory). The controller 58 controls the respective parts based on various types of programs, data and the like stored in the memory. In particular, the controller 58 executes a series of data processing of calculating data or performing processes based on various types of programs, data, or the like, and image display processing of displaying images, and so on.

The restoring part 59 restores original enhanced image data D1 from the respective single image data D2 with reference to incidental information J1 stored in association with the single image data D2 obtained by splitting. When image data (enhanced image dada D1 or single image data D2) of a patient (subject) is received, the restoring part 59 restores single image data D2 that is a past image of the patient, into enhanced image data D1.

Next, a medical image storage operation and a medical image display operation performed by the medical image storage device 5 will be described referring to FIG. 7 and FIG. 8.

Figure 7:
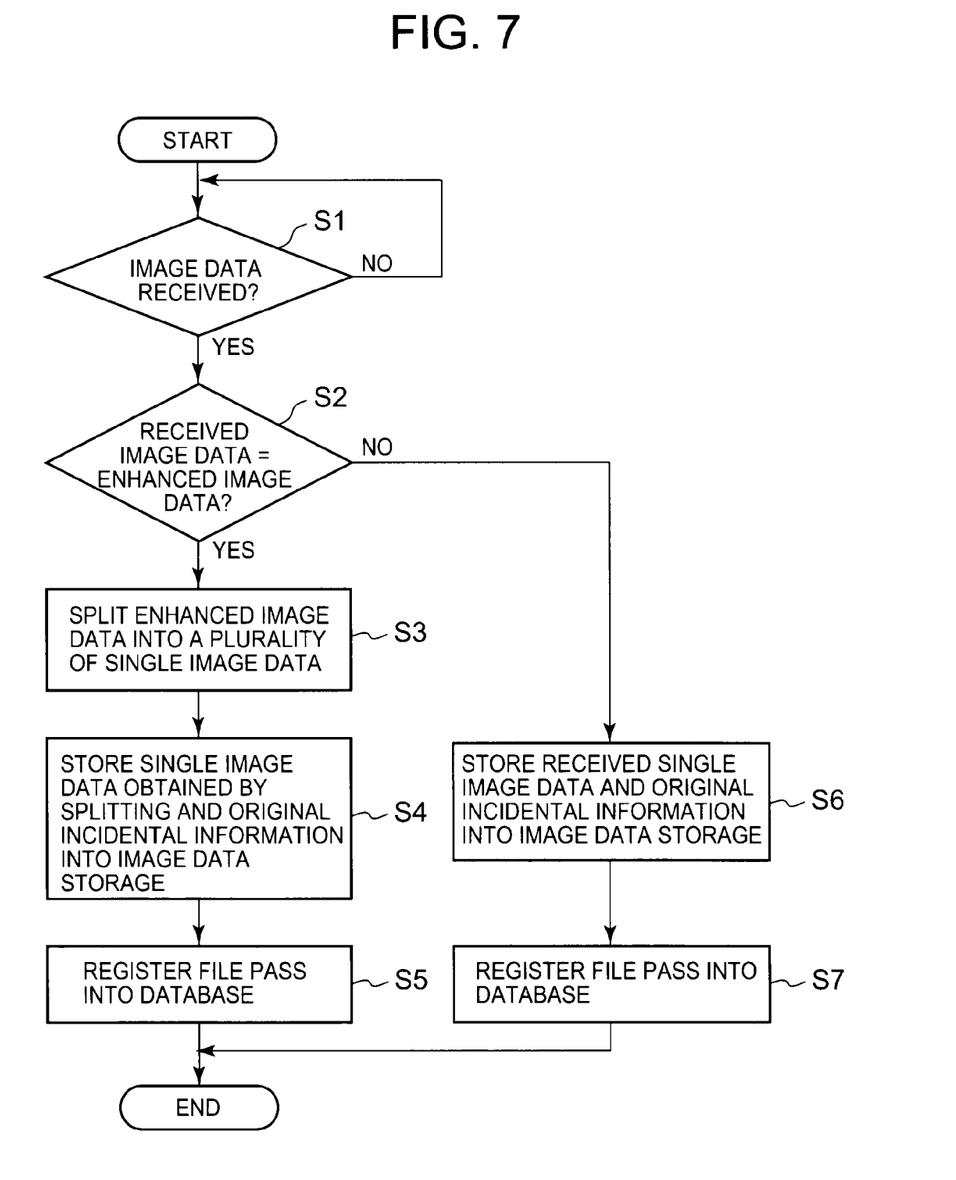
FIG. 7 is a flowchart showing the flow of a medical image storing operation performed by the medical image storage device.

As shown in FIG. 7, in the medical image storage operation, the medical image storage device 5 waits for the receiver 51 to receive image data from the medical imaging device 2 (NO in Step S1), and when the receiver 51 receives the image data from the medical imaging device 2 (YES in Step S1), the image data analyzer 52a determines whether the received image data is enhanced image data D1 (Step S2).

In a case where the received image data is determined to be enhanced image data D1 (YES in Step S2), the enhanced data splitter 52c splits the received enhanced image data D1 into a plurality of single image data D2 based on system information J4 of the enhanced image data D1, and incidental information J1 of the enhanced image data D1 is retained (Step S3: refer to FIG. 3). Here, based on image attribute information J3 within system information of the received enhanced image data D1, system information J4 corresponding to the image attribute information J3 is specified from the system information table T, and a splitting process of splitting the received enhanced image data D1 into a plurality of single image data D2 is conducted based on the specified system information J4. In the splitting process, an image G contained in the enhanced image data D1 is split, and information for identifying the positioning is added to each of the split images G. Then, the medical image storage device 5 stores the incidental information (original incidental information) J1 of the plurality of split single image data D2 and the enhanced image data D1 in the image data storage 54 (Step S4), and registers file paths thereof into the database 53 (Step S5), thereby ending the process.

On the other hand, in a case where the received image data is determined to be not enhanced image data D1, namely, the received image data is determined to be normal image data (single image data D2) (NO in Step S2), the received single image data D2 and the incidental information (original incidental information) J2 of the single image data D2 are stored in the image data storage 54 as they are (Step S6), and file paths thereof are registered in the database 53 (Step S7), whereby the process is ended.

Figure 8:
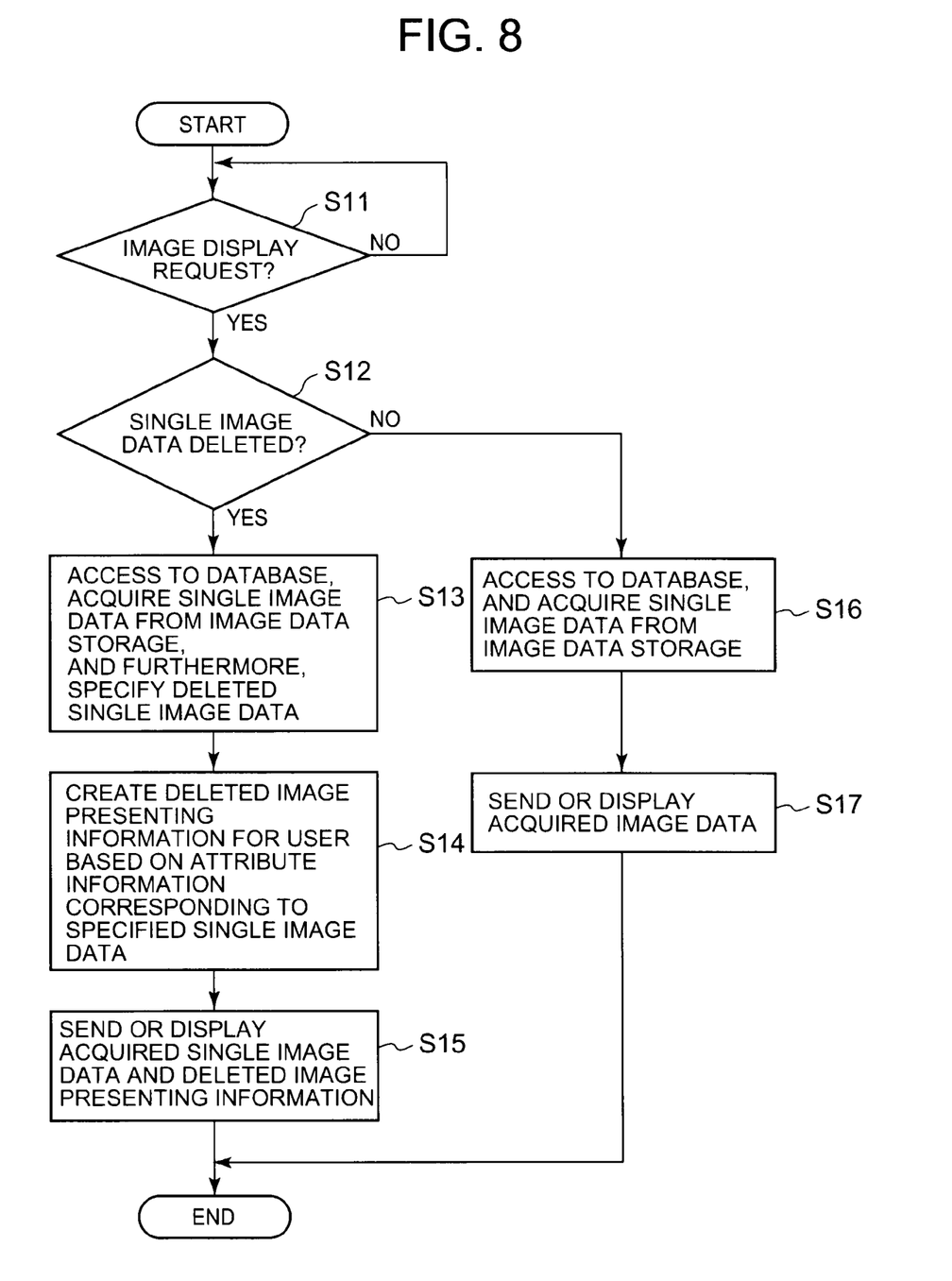
FIG. 8 is a flowchart showing the flow of a medical image displaying operation performed by the medical image storage device.

Next, as shown in FIG. 8, in the medical image display operation, the medical image storage device 5 waits for the receiver 51 to receive an image display request (NO in Step S11), and determines whether single image data D2 has been deleted within image data (normal image data and a plurality of single image data D2) stored in the image data storage 54 (Step S12) when the receiver 51 receives an image display request (request signal) from the medical image observation device 4 or an image display request (request signal) through an input operation to the input part 57 (YES in Step S11). The determination is made based on deletion information embedded in the incidental information J2 of the single image data D2.

In a case where it is determined that single image data D2 has been deleted (YES in Step S12), the single image data D2 subjected to the request is acquired from the image data storage 54 by accessing the database 53, and furthermore, the deleted single image data D2 is specified based on the deletion information embedded in the incidental information J2 of the single image data D2 (Step S13). Deleted image presenting information for the user is created based on the incidental information J2 of the specified single image data D2 (Step S14), and the acquired single image data D2 and the created deleted image presenting information are sent to the medical image observation device 4 by the transmitter 55, or displayed by the display 56 (Step S15), whereby the processes is ended. Consequently, a medical image and a deleted image presenting information are displayed in the medical image observation device 4 or in the display 56.

For example, in a case where an image display request for displaying the images 1-4 is received, as shown in FIG. 5, the respective single image data D2 of the image 1, 2 and 4 are sent either to the medical image observation device 4 or to the display 56, the images 1, 2 and as image 4 are displayed either by the medical image observation device 4 or by the display 56, and further, text such as "third image: automatically deleted" is displayed. Thus, the user is informed that the image 3 has been deleted.

On the other hand, in a case where it is determined that the single image data D2 has not been deleted (NO in Step S12), the single image data D2 subjected to the request is acquired from the image data storage 54 (Step S16) by accessing the database 53. Then, the acquired single image data D2 is sent to the medical image observation device 4 by the transmitter 55, or is displayed by the display 56 (Step S17), whereby the process is ended. Thus, the medical image D2 is displayed in the medical image observation device 4 or in the display 56.

For example, in a case where an image display request for displaying images 5-8 is received, each of the single image data D2 of the images 5-8 is sent either to the medical image observation device 4 or the display 56, and the images 5-8 are displayed by the medical image observation device 4 or the display 56.

The image display request includes: a display request based on an operation of selecting a desired image from an image list (including a patient list, an examination list, etc.) displayed by the medical image observation device 4; a display request based on image display function starting information for reading out, from the image data storage 54, single image data included in a diagnostic finding report created by the medical-report creation supporting device 3; and a display request based on an operation of starting the image display function by the image display function starting information containing location information of an image having been attached to the diagnostic finding report for a reference. Besides, the image display request includes any display requests for displaying images in the medical image observation device 4.

As described above, according to the embodiment of the present invention, the medical image storage device 5 splits the received enhanced image data D1 into a plurality of single image data D2 based on the system information J4 of the received enhanced image data D1. Then, the medical image storage device 5 stores the single image data D2. Consequently, the medical image observation device 4 capable of recognizing single image data D2 can properly recognize the single image data D2, so that the medical image observation device 4 can accurately display medical images based on the respective single image data D2. Therefore, it becomes possible to cause the medical image observation device 4 to accurately display images without depending on the system of the enhanced image data D1. Particularly, even if the systems of the enhanced image data D1 vary depending on the modality types, manufactures or versions, the medical image observation device 4 can properly recognize the single image data D2. In addition, an old style medical image observation device 4 that is not compliant with enhanced image data D1 is also able to accurately display medical images based on single image data D2.

Furthermore, the system information J4 corresponding to the image attribute information J3 of the received enhanced image data D1 is specified based on information associating the image attribute information J3 of the enhanced image data D1 with the system information J4 (for example, system information table T). Then, the received enhanced image data D1 is split into a plurality of single image data D2 based on the specified system information J4. Consequently, the system information J4 is specified in accordance with various image attribute information J3, so that enhanced image data D1 can be split into a plurality of single image data D2 in accordance with a large number of medical imaging devices 2.

In a case where the system information J4 is included in the incidental information J1 attached to a plurality of medical images of the received enhanced image data D1, it is possible to execute the splitting process based on the system information J4 within the received incidental information J1 without the need for the system information table T, and it is possible to acquire the system information J4.

Further, by splitting the received enhanced image data D1 into a plurality of single image data D2 so that it is possible to manage the plurality of single image data D2 by classification units provided by the system information J4, it is possible, even when the medical image observation device 4 makes a request for medical images by classification units, to provide single image data D2 by classification units in response to the request.

Furthermore, because the plurality of single image data D2 are provided by the DICOM standard, the medical image observation device 4 compliant with the DICOM standard can properly recognize the single image data D2, and therefore, accurately display a medical image based on the single image data D2.

In addition, by storing the incidental information J1 attached to the plurality of medical images of the enhanced image data D1 so as to be associated with the plurality of split single image data D2, it is possible to restore each of the single image data D2 back into the original enhanced image data D1 when necessary. As a result, it becomes possible to send each of the single image data D2 after restoring to the original enhanced image data D1 on the medical image observation device 4 capable of recognizing enhanced image data D1, a large volume of images may be sent at a high speed.

Therefore, because the plurality of single image data D2 are restored into the enhanced image data D1 based on the incidental information J1 of the enhanced image data D1, it becomes possible to prepare image data for a high speed access when necessary, and thus, images may be displayed faster. In the case of this restoration, for example, a subject related to the received enhanced image data D1 or single image data D2 may be specified to restore a plurality of single image data D2 related to the specified subject to the enhanced image data D1. Consequently, in the event that image data (enhanced image data D1 or single image data D2) of a patient (subject) is received, it is possible, by taking this event as a trigger, to restore the single image data D2 that is a past image of the patient into enhanced image data D1 if possible. As a result, because it becomes possible to prepare image data for a high speed access when needed, images may be displayed faster.

Moreover, by deleting a medical image of single image data D1 having been stored for a predetermined period, based on the set information for setting the timing of deleting a medical image, a medical image of the single image data D1 having been stored for a predetermined period, for example, for several weeks or one month is deleted, and it becomes possible to avoid storing unnecessary medical images, so that it is possible to effectively use the capacity of the storage 54.

Furthermore, by adding deletion information representing deletion of a medical image to the incidental information J2 of single image data D2 corresponding to the deleted medical image, it becomes possible to use the deletion information, so that it is possible, based on the deletion information, for example, display deleted image-presenting information such as an image indicating the deletion of the medical image. As a result, it is possible to inform the user of the deletion of the medical image.

In addition, by eliminating inconsistencies of the incidental information J1 of enhanced image data D1 corresponding to the single image data D2 of the deleted medical image, consistencies between the original enhanced image data D1 and the corresponding each set of single image data D2 may be maintained.

Another Embodiment

The present invention is not limited to the aforementioned embodiment, and it is possible to change in various manners within the scope of the gist.

For example, the splitting process is executed for received enhanced image data D1 in the aforementioned embodiment, but instead, in such a case that received enhanced image data D1 is stored and thereafter the stored enhanced image data D1 is sent, the splitting process may be executed for the stored enhanced image data D1. In this case, a plurality of single image data D2 with larger data volume than the enhanced image data D1 before the splitting process are not stored in the image data storage 54, and the enhanced image data D1 before the splitting process is stored in the image data storage 54, whereby it is possible to effectively use the capacity of the image data storage 54. Here, in response to an image display request or the like, the splitting process is executed for the stored enhanced image data D1, and the plurality of single image data D2 obtained by splitting are sent, so that it is possible to obtain the same effect as in the aforementioned embodiment.

Further, a medical image of single image data D2 is deleted regardless of a classification unit in the aforementioned embodiment, but instead, for example, the single image data D2 may be deleted collectively by classification unit such as series.

Furthermore, in the aforementioned embodiment, deleted image presenting information is displayed in the medical image observation device 4 or the display 56 to inform that an unnecessary medical image has been deleted, but instead, for example, it may be informed by sound like voice.

Finally, inconsistencies of incidental information J1 of enhanced image data D1 that corresponds to single image data D2 of the deleted medical image are solved in the aforementioned embodiment, but instead, the inconsistencies may be left without being solved in a case where the inconsistencies make no effect.

What is claimed is:

1. A medical image storage device, comprising:
a receiver that receives enhanced image data having a plurality of medical images; and
a splitter that splits the received enhanced image data into a plurality of single image data each having only one medical image, based on system information of the received enhanced image data,
wherein the splitter specifies, based on information associating image attribute information of the enhanced image data with the system information, the system information corresponding to the image attribute information of the received enhanced image data, and splits the received enhanced image data into the plurality of single image data based on the specified system information.

2. The medical image storage device according to claim 1, comprising a storage that stores the plurality of single image data obtained by splitting.

3. The medical image storage device according to claim 1, comprising a storage that stores the received enhanced image data, wherein at the time of sending the stored enhanced image data, the splitter splits the stored enhanced image data into the plurality of single image data.

4. The medical image storage device according to claim 1, wherein the splitter splits the received enhanced image data into the plurality of single image data so that it is possible to manage the plurality of single image data by classification units provided by the system information.

5. The medical image storage device according to claim 1, wherein the splitter attaches, to the single image data obtained by splitting, information for identifying positioning of the single image data, based on system information.

6. The medical image storage device according to claim 1, wherein the system information is included in incidental information of the received enhanced image data.

7. The medical image storage device according to claim 1, wherein the plurality of single image data are provided by DICOM standard.

8. The medical image storage device according to claim 2, wherein the storage stores incidental information of the enhanced image data in association with the plurality of single image data obtained by splitting.

9. A medical image storage device, comprising:
a receiver that receives enhanced image data having a plurality of medical images;
a splitter that splits the received enhanced image data into a plurality of single image data each having only one medical image, based on system information of the received enhanced image data;
a storage that stores the plurality of single image data obtained by splitting;
a restoring part that restores the plurality of single image data into the enhanced image data, based on the stored incidental information in association with the plurality of single image data obtained by splitting; and
wherein the storage stores incidental information of the enhanced image data in association with the plurality of single image data obtained by splitting.

10. The medical image storage device according to claim 9, wherein: the receiver receives the single image data or the enhanced image data; and
the restoring part specifies a subject related to the received single image data or enhanced image data, and restores the plurality of single image data related to the specified subject into the enhanced image data.

11. The medical image storage device according to claim 1, comprising a deleting part that deletes the medical image of the single image data having been stored for a predetermined period, based on set information that sets timing to delete the medical image.

12. A medical image storage device, comprising:
a receiver that receives enhanced image data having a plurality of medical images;
a splitter that splits the received enhanced image data into a plurality of single image data each having only one medical image, based on system information of the received enhanced image data;
a deleting part that deletes the medical image of the single image data having been stored for a predetermined period, based on set information that sets timing to delete the medical image;
wherein the deleting part adds deletion information representing that the medical image has been deleted, to incidental information of the single image data that corresponds to the deleted medical image.

13. A medical image storage device, comprising:
a receiver that receives enhanced image data having a plurality of medical images;
a splitter that splits the received enhanced image data into a plurality of single image data each having only one medical image, based on system information of the received enhanced image data;
a deleting part that deletes the medical image of the single image data having been stored for a predetermined period, based on set information that sets timing to delete the medical image;
wherein the deleting part deletes information for identifying the deleted medical image from incidental information of the enhanced image data that corresponds to the single image data of the deleted medical image, and advances information for identifying the medical images arranged after the deleted medical image.

14. The medical image storage device according to claim 1, wherein the image attribute information comprises a modality name, a manufacture name, a version of software, communication information, and image classification.

* * * * *